(12) United States Patent
Saudan et al.

(10) Patent No.: US 8,871,982 B2
(45) Date of Patent: Oct. 28, 2014

(54) HYDROGENATION OF DIENALS WITH RHODIUM COMPLEXES UNDER CARBON MONOXIDE FREE ATMOSPHERE

(75) Inventors: Christophe Saudan, Geneva (CH); Michel Alfred Joseph Saudan, legal representative, Geneva (CH); Sylvia Joyeuse Adélaïde Ada Saudan, legal representative, Geneva (CH); Lionel Saudan, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/000,805

(22) PCT Filed: Feb. 17, 2012

(86) PCT No.: PCT/EP2012/052733
§ 371 (c)(1),
(2), (4) Date: Aug. 21, 2013

(87) PCT Pub. No.: WO2012/150053
PCT Pub. Date: Nov. 8, 2012

(65) Prior Publication Data
US 2013/0331611 A1     Dec. 12, 2013

(30) Foreign Application Priority Data
Feb. 22, 2011 (EP) .................................... 11155391

(51) Int. Cl.
*C07C 45/62* (2006.01)

(52) U.S. Cl.
CPC .................................... *C07C 45/62* (2013.01)
USPC ............................. 568/434; 568/446; 568/459

(58) Field of Classification Search
USPC ........................................ 568/434, 446, 459
See application file for complete search history.

(56) References Cited

U.S. PATENT DOCUMENTS 4,237,072 A     12/1980 Aviron-Violet et al.

OTHER PUBLICATIONS

International Search Report and Written Opinion, application PCT/EP2012/052733, mailed Apr. 19, 2012.
Bronger et al., Adv. Synth. & Catal. 2004, 346, 7, 789-799.
Bronger et al., Organometallics, 2003, 22, 5358.
Burk et al., J. Am. Chem. Soc., 1998, 120, 657-663.
Chapuis et al., Helv. Chim. Acta, vol. 84 (2001), 230.
Dang et al., Journ. of Mol. Catalysis, 1982, vol. 16, n° 1, 51-59.
Dierkes et al., J. Chem. Soc., Dalton Trans, 1999, 1519.
Kranenburg et al., Organometallics, 1995,14, 3081-3089.
Ojima et al., Organometallics, 1982, vol. 1, 1390-1399.
Ojima et al., Tetrah. Lett., 1972, vol. 13, n° 49, 5035-5038.
Ooi et al., Chemistry Letters, 1998, vol. 27, n° 5, 403-404.
Trost et al., Comprehensive Organic Chemistry, 1991, 535 & 555.
van Leeuwen et al., Chem. Rev. 2000, 100, 2741-2769.

*Primary Examiner* — Sikarl Witherspoon
(74) *Attorney, Agent, or Firm* — Winston & Strawn LLP

(57) ABSTRACT

The present invention relates to the field of catalytic hydrogenation and, more particularly, to a process for the reduction by hydrogenation, using molecular $H_2$, of a $C_6$-$C_{20}$ conjugated dienal into the corresponding deconjugated enal, characterized in that said process is carried out in the presence of a catalytic system comprising at least a base and at least one complex in the form of a rhodium complex comprising a $C_{34}$-$C_{60}$ bidentate diphosphine ligand (L2) coordinating the rhodium.

18 Claims, No Drawings

HYDROGENATION OF DIENALS WITH RHODIUM COMPLEXES UNDER CARBON MONOXIDE FREE ATMOSPHERE

TECHNICAL FIELD

The present invention relates to the field of catalytic hydrogenation and, more particularly, to the use of a catalytic system comprising a specific rhodium complex in hydrogenation processes for the reduction of a conjugated dienal into the corresponding deconjugated enal.

PRIOR ART

The direct selective α-β hydrogenation, i.e. of a specific C=C bond, of a conjugated dienal (α,γ-dienal) is a challenging target. Indeed, the hydrogenation may take place at three different sites (two C=C and one C=O). Moreover, in order to render such process attracting for an industrial purpose, it is preferable to achieve the hydrogenation with an acceptable conversion and with a reasonable turn-over (complex load and reaction time).

In the prior art, it is possible to find a number of examples of selective α-β hydrogenation of conjugated enals, in particular of geranial/neral, into the respective aldehydes. One may cite Dang T. G et al. in *J. of Mol. Catalysis*, 1982, 16, 51, wherein geranial is reduced into the aldehyde citronellal. Other similar references are U.S. Pat. No. 4,237,072 (example 1) or *Helv. Chem. Acta*, 2001, 230 (footnote 4).

Trost et al. (in *Comprehensive Organic Chem.*, 1991, vol 8, p. 535) report the reduction of a conjugated enone into a ketone, using conditions which do not work with enal as even mentioned by the author.

However said documents show that long reaction times are required to perform such simple selectivity with acceptable yields, e.g. from 4 to 24 hours. Furthermore, such references are totally silent on the possibility to apply such systems on the selective α-β hydrogenation of a conjugated dienal as substrate.

Only one example of selective α-β hydrogenation of a conjugated diene system is reported in the literature (see Burk M. J. et al in *J. Am. Chem. Soc.*, 1998, 120, 657). In this document, it is performed an α-β hydrogenation of a α,γ-dienamide ester, but it is specified that the acetamido group of the substrate is essential to ensure a high selectivity (or enhance reactivity of the targeted C=C double bond). Therefore said document cannot assist the person skilled in the art to conceive the present invention.

Ojima et al. (in *Organomet.* 1982, 1390) report the reduction of a conjugated dienone, using a rhodium, complex and a silane as reducing agent, but the product obtained being an allyl alcohol or a deconjugated ketone depending on the nature of silane reagent.

None of the prior art documents reports the use of the specific catalytic system of the present invention, in particular the use of a base.

Therefore there is still a need for a process allowing the selective α-β hydrogenation of a α,γ-dienal, and if possible within reaction conditions which are applicable industrially.

DESCRIPTION OF THE INVENTION

In order to overcome the problems aforementioned, the present invention relates to processes for the reduction by hydrogenation, i.e. using molecular $H_2$, of a $C_6$-$C_{20}$ conjugated dienal into the corresponding deconjugated enal, characterized in that said process is carried out in the presence of a catalytic system comprising at least a base and at least one complex in the form of a rhodium complex comprising a $C_{34}$-$C_{60}$ bidentate diphosphine ligand (L2) coordinating the rhodium.

According to a particular embodiment of the invention, the conjugated dienal is of formula

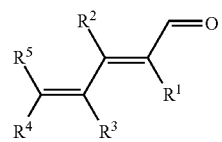

(I)

wherein, when taken separately, each of $R^1$, $R^2$, $R^3$, $R^4$ and $R^5$ represents, independently of each other, a hydrogen atom, a phenyl group optionally substituted or a $C_{1-8}$ alkyl, alkenyl, cycloalkyl or cycloalkenyl group optionally substituted, provided that at least one of said $R^1$, $R^2$, $R^3$, $R^4$ and $R^5$ is not a hydrogen atom; $R^1$ and $R^2$ or $R^2$ and $R^3$ or $R^3$ and $R^4$, when taken together, represent a $C_{3-4}$ alkadienyl or alkenediyl group optionally substituted; $R^1$ and $R^3$ or $R^2$ and $R^5$, when taken together, represent a $C_{2-3}$ alkadienyl or alkenediyl group optionally substituted; $R^4$ and $R^5$, when taken together, represent a $C_{4-5}$ alkadienyl or alkenediyl group optionally substituted;

into a deconjugated enal of formula

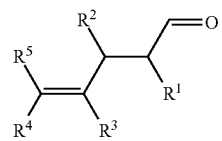

(II)

wherein $R^1$ to $R^5$ are defined as in formula (I);
said process being carried out in the presence of a catalytic system comprising:
 at least a base; and
 at least one Rh(I) complex obtainable by reacting a suitable Rh(I) precursor and a $C_{34}$-$C_{60}$ bidentate diphosphine ligand (L2) having a natural bite-angle comprised between 93° and 130°.

By the expression "natural bite-angle" it is understood the usual meaning in the art, e.g. as defined in P. W. N. M. van Leeuwen, P. C. J. Kamer, J. N. H. Reek, P. Dierkes, *Chem. Rev.* 2000, 2741.

Possible substituents of $R^1$ to $R^5$ are one phenyl group or one, two or three $COOR^7$, $OR^6$ or $R^7$ groups, in which $R^6$ is a hydrogen atom or a $R^7$ group, $R^7$ representing a $C_{1-4}$ linear or branched alkyl or alkenyl group. According to any one of the embodiments of the invention, only one or two of said $R^1$ to $R^5$ are optionally substituted.

It is understood that said compounds (II) can be in a racemic or optically active form, depending on the nature of the substrate and on the complex used.

It is understood that by "alkenyl", "cycloalkenyl" or "alkenediyl" group it is meant here the usual meaning in the art, which is an unsaturated group wherein the unsaturation cannot be conjugated to the carbon-carbon double bonds of the conjugated dienal.

It is understood that by "conjugated dienal" it is meant a compound possessing at least two carbon-carbon double bonds and an aldehyde functional group, the three of them being conjugated, as indicated in formula (I). The term "conjugated dienal" is therefore understood as optionally comprising also compounds having additional non-aromatic carbon-carbon double bonds provided that said additional carbon-carbon double bonds are not conjugated to the ones of the dienal system.

It is understood that by "deconjugated enal" it is meant a compound possessing at least one γ-δ carbon-carbon double bond and an aldehyde functional group, as indicated in formula (II). The term "deconjugated enal" is therefore understood as optionally comprising also compounds having additional carbon-carbon double bonds provided that said additional non-aromatic carbon-carbon double bonds are not conjugated to the one of the enal system.

According to an embodiment of the invention, the compounds of formula (I) and (II) is a $C_6$-$C_{15}$ compound, and in particular one may cite those wherein, when taken separately, each of $R^1$, $R^2$, $R^3$, $R^4$ and $R^5$ represents, independently of each other, a hydrogen atom, a phenyl group optionally substituted or a $C_{1-4}$ alkyl or cycloalkyl group optionally substituted, provided that at least one of said $R^1$, $R^2$, $R^3$, $R^4$ and $R^5$ is not a hydrogen atom; $R^3$ and $R^4$, when taken together, represent a $C_{3-4}$ alkadienyl group optionally substituted; $R^4$ and $R^5$, when taken together, represent a $C_{4-5}$ alkadienyl group optionally substituted.

According to any one of the above embodiments, when taken separately, said $R^1$ represents a hydrogen atom.

According to any one of the above embodiments, when taken separately, said $R^2$ represents a hydrogen atom.

According to any one of the above embodiments, when taken separately, said $R^3$ represents a hydrogen atom or a methyl or ethyl group or a phenyl group optionally substituted.

According to any one of the above embodiments, when taken separately, said $R^4$ represents a hydrogen atom or a methyl or ethyl group or a cyclohexyl or cyclopentyl group or a phenyl group optionally substituted.

According to any one of the above embodiments, when taken separately, said $R^5$ represents a hydrogen atom or a methyl or ethyl group or a cyclohexyl or cyclopentyl group or a phenyl group optionally substituted.

According to any one of the above embodiments, when taken together, said $R^3$ and $R^4$, when taken together, represent a $C_4$ alkadienyl group optionally substituted.

According to any one of the above embodiments, when taken together, said $R^4$ and $R^5$, when taken together, represent a $C_5$ alkadienyl group optionally substituted.

According to any one of the above embodiments, the substrate of formula (I) is one wherein $R^1$, $R^2$ represent each a hydrogen atom, $R^3$, $R^4$, $R^5$ represent each a hydrogen atom or a methyl or ethyl group or a cyclohexyl or phenyl group optionally substituted, provided that at least one of said $R^1$, $R^2$, $R^3$, $R^4$ and $R^5$ is not a hydrogen atom; $R^3$ and $R^4$, when taken together, represent a $C_4$ alkadienyl group optionally substituted.

According to any one of the above embodiments, the substrate of formula (I) is one wherein at least one or two of said $R^1$, $R^2$, $R^3$, $R^4$ and $R^5$ is a hydrogen atom.

According to any one of the above embodiments, the substrate of formula (I) is one wherein two or three of said $R^1$, $R^2$, $R^3$, $R^4$ and $R^5$ are a hydrogen atom.

According to any one of the above embodiments, the substituents of said $R^1$ to $R^5$ are one phenyl group or one or two $OR^6$ or $R^7$ groups, in which $R^6$ is a hydrogen atom or a $R^7$ group, $R^7$ representing a $C_{1-4}$ linear or branched alkyl group. Preferably said substituents are a $OR^7$ or $R^7$ group. According to any one of the embodiments of the invention, only one or two of said $R^1$ to $R^5$ are optionally substituted.

According to a further embodiment of the invention, the substrate is a conjugated dienal that will provide a deconjugated enal that is useful in the pharmaceutical, agrochemical or perfumery industry as final product or as an intermediate. Particularly preferred substrate is a conjugated dienal that will provide a deconjugated enal which is useful in the perfumery industry as final product or as an intermediate.

Non-limiting examples of substrates are the following: (2E,4E)-4-methyl-5-(p-tolyl)penta-2,4-dienal, (2E,4E)-5-phenylpenta-2,4-dienal, (2E,4E)-5-phenylhexa-2,4-dienal, (2E,4E)-4-methyl-5-phenylpenta-2,4-dienal, (2E,4E)-2-methyl-5-phenylpenta-2,4-dienal, (2E,4Z)-4-phenylhexa-2,4-dienal, (E)-3-(4-(tert-butyl)cyclohex-1-en-1-yl)acrylaldehyde, (E)-5-cyclohexyl-4-methylpent-4-enal or (E)-5-cyclohexyl-2,4-dimethylpent-4-enal.

According to a particular aspect of any one of the invention's embodiments, the invention's process is also characterized by providing compound (II) with a selectivity above 40%, preferably above 60, more preferably above 80%.

According to a particular aspect of any one of the invention's embodiments, the invention's process is also characterized by providing compound (II) with a conversion of the staring compound of above 60%, preferably above 70%.

Wherein by "deconjugated enal" it is meant the compound (II), by "aldehyde" it is meant the compound (I) wherein both carbon-carbon double bonds have been reduced and by "alcohol" it is meant the aldehyde wherein the carbonyl has also been reduced.

The hydrogenation reaction can be carried out in the presence or absence of a solvent. In a particular embodiment of the invention, the process is carried out in the presence of a solvent (in general for practical reasons), and any solvent current in hydrogenation reactions can be used for the purposes of the invention. Non-limiting examples include $C_{6-10}$ aromatic solvents such as toluene or xylene, $C_{1-2}$ halogenated hydrocarbon such as $CH_2Cl_2$, $C_{5-8}$ hydrocarbon solvents such as hexane or cyclohexane, $C_{4-9}$ ethers such as tetrahydrofuran or MTBE, $C_{3-9}$ esters such as ethyl or methyl acetate, $C_{3-6}$ ketones such as acetone, polar solvents such as $C_{1-5}$ primary or secondary alcohols such as isopropanol or ethanol, or mixtures thereof. The choice of the solvent is a function of the nature of the substrate, of the base and of the complex and the person skilled in the art is well able to select the most convenient solvent in each case to optimize the hydrogenation reaction.

In the hydrogenation process of the invention, the reaction can be carried out under an atmosphere of pure $H_2$ or under a mixture of hydrogen and of at least an inert gas, such as $N_2$ or Ar. Preferably, the atmosphere of the reaction medium is CO-free, e.g. the amount of CO present is below 1 ppm. It is understood that in any case the reaction medium is preferably supplied with at least a steochiometric amount of $H_2$ relative to the substrate; if less than a steochiometric amount of $H_2$ then it is achieved only a partial conversion of the substrate. In any case, as non-limiting example, one may cite typical $H_2$ pressure comprised between $10^5$ Pa and $80 \times 10^5$ Pa (1 to 80 bars) or even more if desired. Again, a person skilled in the art is well able to adjust the pressure as a function of the complex load and of the dilution of the substrate in the solvent. As examples, one can cite typical pressures of 3 to $50 \times 10^5$ Pa (3 to 50 bar), or even of 5 to $20 \times 10^5$ Pa (5 to 20 bar).

The temperature at which the hydrogenation can be carried out is comprised between 0° C. and 100° C., preferably in the range of between 10° C. and 80° C. Of course, a person skilled in the art is also able to select the preferred temperature as a function of the melting and boiling point of the starting and final products as well as the desired time of reaction or conversion.

As mentioned above, the present invention requires the use of a particular catalytic system comprising at least a base and at least a Rh complex. The base and the Rh complex can be premixed, under hydrogen or inert atmosphere, prior to the use of the catalytic system in the process, or they can be added separately into the reaction medium.

Said base can be any organic or inorganic base having preferentially a $pK_a$ (of the protonated base) comprised between about 2 and 12, in particular between about 2.5 and 12, or even between about 2.8 and 10.5. It is understood that herein by "pKa" it is meant the usual meaning in the art, e.g. the constant measured in water under standard conditions as for example reported in http://www.chem.wisc.edu/areas/reich/pkatable/index.htm.

According to any one of the above embodiments, said base is : as inorganic base an alkaline or $C_{4-16}$ ammonium carbonate or bicarbonate, a basic alox, a siliconate (i.e. silicium derivatives having $SiO^-$ or $SiRO^-$ groups), or an alkaline alkaline-earth or $C_{4-16}$ ammonium fluoride; as organic base an alkaline or $C_{4-16}$ ammonium $C_{2-10}$ carboxylate, or an alkaline or $C_{4-16}$ ammonium $C_{6-10}$ phenolate optionally substituted, an alkaline or $C_{4-16}$ ammonium $C_{5-15}$ 1,3-diketonate, or a $C_{8-10}$ bicyclic amidine.

According to any one of the above embodiments, said base is a carbonate, or a fluoride, or a carboxylate such as an acetate or benzoate, or a $C_{5-15}$ 1,3-diketonate such as an acetylacetonate or a 5-oxohept-3-en-3-olate, or phenolate such as a phenolate or a naphtholate.

According to any one of the above embodiments, said base is sodium acetate, potassium acetate, sodium benzoate, potassium benzoate, sodium (Z)-4-oxopent-2-en-2-olate, sodium (Z)-2,2,6,6-tetramethyl-5-oxohept-3-en-3-olate, sodium phenolate, sodium 2,6-di-tert-butyl-4-methylphenolate, cesium carbonate.

According to any one of the above embodiments, said base is a potassium salt.

According to any one of the above embodiments, the Rh(I) complex is a compound obtainable by reacting together:
a $C_{34}$-$C_{60}$ bidentate diphosphine ligand (L2) having a natural bite-angle comprised between 93° and 130°; and
a suitable Rh(I) precursor of formula

  (1)

or

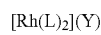  (1')

wherein r is 0 or 1, v is 0, 1 or 2;
L represents a $C_{5-14}$ hydrocarbon diene;
S represents a coordinated molecule of a polar organic solvent or water; and
Y represents a mono-anion.

The precursor of formula (1) or (1') can be in a monomeric, dimeric or oligomeric form.

The preparation of the Rh(I) complex is preferably carried out in the presence a solvent. In a particular embodiment of the invention, said solvent is the same optionally used in the hydrogenation process. However other solvents can be used, and as non limiting examples one may cite $C_{6-10}$ aromatic solvents such as toluene or xylene, $C_{5-8}$ hydrocarbon solvents such as hexane or cyclohexane, $C_{4-9}$ ethers such as tetrahydrofuran or MTBE, polar solvents such as $C_{1-5}$ primary or secondary alcohols such as isopropanol or ethanol, dichloromethane, water or mixtures thereof. The choice of the solvent is a function of the nature of the substrate, of the base and of the complex and the person skilled in the art is well able to select the most convenient solvent in each case to optimize the hydrogenation reaction.

The preparation of the Rh(I) complex can be carried out under an inert, or an essentially carbon monoxide and oxygen free atmosphere, e.g. the amount of CO and $O_2$ present is below 1 ppm. A person skilled in the art knows what is meant by an inert atmosphere. Non-limiting examples of such atmosphere are a nitrogen or argon atmosphere.

In the preparation of the Rh(I) complex, the temperature of the process can be comprised between 0° C. and 100° C., preferably in the range of between 10° C. and 60° C. Of course, a person skilled in the art is also able to select the preferred temperature as a function of the melting and boiling point of the starting and final products as well as the desired time of reaction or conversion.

According to a particular embodiment of the invention, said S is the solvent used as process solvent, including water. According to a particular embodiment of the invention, said S is water or an organic solvent having a dielectric constant E comprised between about 5 and 40, said constant being measured at standard conditions. Said constant can be retrieved in chemical Handbooks such as "Handbook of Chemistry and Physics", 87$^{th}$ edition, 2006-2007, page 15-13 to 15-23, ISBN 978-0-8493-0487-3, or such as March's "Advanced Organic Chemistry" 5$^{th}$ edition, ISBN 0-471-58589-0, or any other similar reference.

As typical, non-limiting examples one may cite the following examples of S : a $C_{4-7}$ ether (such as tetrahydrofurane (THF) or methyl tertbutyl ether (MTBE)), or a $C_{1-4}$ alcohol (such as ethanol or isopropanol), or water or N,N-dimethylformamide (DMF).

According to a particular embodiment, it is believed that the Rh(I) complex can be described as having the formula

  (2)

wherein L2, L and Y have the same meaning as for formula (1).

According to any one of the above embodiments, said diene L represents a linear or branched $C_5$-$C_{14}$ hydrocarbon compound comprising two carbon-carbon double bonds or a cyclic $C_7$-$C_{14}$ hydrocarbon compound comprising two carbon-carbon double bonds.

According to a particular embodiment of the invention, said L is a $C_7$-$C_{12}$, or a $C_7$-$C_{10}$, hydrocarbon compound comprising two carbon-carbon double bonds, optionally substituted, e.g. a cyclic $C_7$-$C_{12}$, or a linear or branched $C_7$-$C_{10}$, hydrocarbon compound comprising two carbon-carbon double bonds. As well understood by a person skilled in the art, by "cyclic hydrocarbon" it is understood a group comprising a cyclic moiety.

As non-limiting examples of suitable L, one may cite compounds such as COD (cycloocta-1,5-diene) or NBD (norbornadiene), 2,4-dimethyl-1,3-pentadiene or yet cyclohepta-1,4-diene.

The examples of L provided above are applicable for both compounds (1) and (2). Anyhow, as a person skilled in the art would recognise, the diene present in the precursor (1) or (1') will be the same as that of the compound (2).

According to any one of the above embodiments, said Y represents a halide, a $C_{5-15}$ 1,3-diketonate, a $C_1$-$C_8$ alkoxide, $OH^-$, $ClO_4^-$, $BF_4^-$, $PF_6^-$, $SbCl_6^-$, $AsCl_6^-$, $SbF_6^-$, $AsF_6^-$, a $R^dSO_3^-$ wherein $R^d$ is a chlorine of fluoride atom or a $C_1$-$C_8$ alkyl, aryl, fluoroalkyl or fluoroaryl group, or a $BR^e_4^-$ wherein $R^e$ is a phenyl group optionally substituted by one to five groups such as halide atoms and/or methyl and/or $CF_3$ groups.

According to any one of the above embodiments, said Y represents $Cl^-$, acetylacetonate, $BF_4^-$, $PF_6^-$ or $CF_3SO_3^-$. In particular said Y represents $Cl^-$.

The examples of Y provided above are applicable for both compounds (1) and (2). Anyhow, as a person skilled in the art would recognise, the mono-anion present in the precursor (1) will be the same as that of the compound (2). In the case wherein Y is a basic anion having a $pK_a$ comprised within the $pk_a$ range disclosed above for the base, said Y may also serve as at least part of the base added into the catalytic system.

Non-limiting examples of precursors of formula (1) are the following: acetylacetonato(1,5-cyclooctadiene)rhodium(I), bis(1,5-cyclooctadiene)rhodium(I) tetrafluoroborate, bis(1,5-cyclooctadiene)rhodium(I) trifluoromethanesulfonate, bis(1,5-cyclooctadiene)rhodium(I) tetrakis[bis(3,5-trifluoromethyl)phenyl]borate, bis(norbornadiene)rhodium(I) tetrafluoroborate, chlorobis(1,5-cyclooctadiene)rhodium(I) dimer, chloronorbornadienerhodium(I) dimer, di-μ-methoxobis(1,5-cyclooctadiene)dirhodium(I) or hydroxy(1,5-cyclooctadiene)rhodium(I) dimer.

According to any one of the above embodiments, L2 can be a compound of formula $$(R^b)_2P-Q-P(R^b)_2 \quad (A)$$

wherein each $R^b$, taken separately, represents a $C_{6-10}$ aromatic group optionally substituted or a cyclohexyl group optionally substituted, or the two $R^b$ bonded to the same P atom, taken together, represent a 2,2'-oxydiphenyl optionally substituted; and Q represents a $C_{10}$-$C_{16}$ metallocenediyl optionally substituted or a group of formula a)

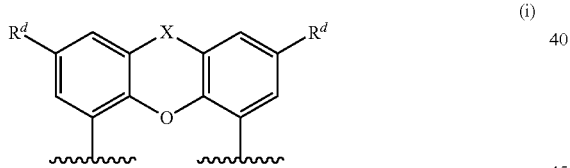

wherein each $R^d$ represents a hydrogen atom or a $C_{1-9}$ alkyl group, and X represents an oxygen or sulfur atom or a $C(R^{10})_2$, $Si(R^{11})_2$ or $NR^{10}$ group, in which $R^{10}$ is a hydrogen atom or a $R^{11}$ group, $R^{11}$ representing a $C_{1-4}$ linear or branched alkyl group, preferably methyl; or b)

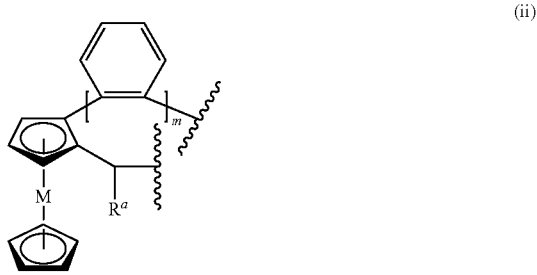

in the form of any one of its enantiomers, and wherein m is 0 or 1, M represents Fe or Ru, and $R^a$ represents a hydrogen atom or a $C_{1-4}$ alkyl group;

and the wavy lines indicate the position of the bond between said Q group and the rest of the compound (A).

According to any one of the above embodiments, Q represents a 1,1'-ferrocenediyl optionally substituted or a group of formula a)

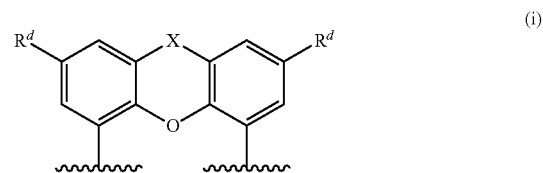

wherein each $R^d$ represents a hydrogen atom or a $C_{1-4}$ alkyl group, and X represents a $C(R^{10})_2$, $Si(R^{11})_2$ or $NR^{10}$ group, in which $R^{10}$ is a hydrogen atom or a $R^{11}$ group, $R^{11}$ representing a $C_{1-4}$ linear or branched alkyl group, preferably methyl; or b)

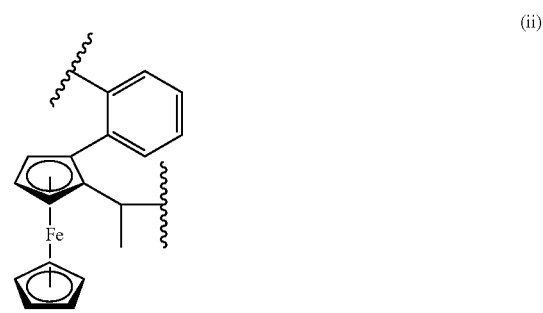

in the form of any one of its enantiomers;

the wavy lines indicate the position of the bond between said Q group and the rest of the compound (A).

According to any one of the above embodiments, in the definition of Q the metallocenediyl is a ferrocenediyl and in particular a 1,1'-diyl group. In formula (II), in particular M is Fe.

According to any one of the above embodiments, each $R^b$ represents a $C_{6-10}$ aromatic group optionally substituted or a cyclohexyl group optionally substituted.

According to any one of the above embodiments, by "aromatic group or ring" it is meant a phenyl or naphthyl group, and in particular a phenyl group.

According to any one of the above embodiments, each $R^b$ represents a phenyl group, a cyclohexyl group, a 3,5-dimethyl-phenyl, a 3,5-di($CF_3$)-phenyl, a 3,5-dimethyl-4-methoxy-phenyl group.

According to any one of the above embodiments, the $R^d$ represents a hydrogen atom.

According to any one of the above embodiments, X represents a $CMe_2$, $SiMe_2$, NH or NMe group.

According to any one of the above embodiments, L2 has a natural bite-angle comprised between 97° and 120°.

According to any one of the above embodiments, non-limiting examples of possible substituents of $R^b$ are one, two, three or four groups selected amongst the halogen atoms, or $C_{1-10}$ alkoxy, alkyl, alkenyl, or perhalo-hydrocarbon group. The expression "perhalo-hydrocarbon" has here the usual meaning in the art, e.g. a group such as $CF_3$ for instance. In particular said substituents are one or two halogen atoms, such as F or Cl, or $C_{1-4}$ alkoxy or alkyl groups, or $CF_3$ groups.

According to any one of the above embodiments, non-limiting examples of possible substituents of the metallocenediyl or 1,1'-ferrocenediyl group are one or two $C_{1-4}$ alkyl groups or a $CR^{d'}PhN(R^{d''})_2$ group, wherein $R^{d'}$ or $R^{d''}$ are a hydrogen atom or a $C_{1-4}$ alkyl group and Ph is a phenyl group optionally substituted as indicated above for $R^c$. In particular, said substituents are one methyl or one $CH(C_6H_5)N(Me)_2$ group.

According to any one of the above embodiments, said $R^b$, metallocenediyl or 1,1'-ferrocenediyl groups, one by one or all together, are non substituted.

According to any one of the above embodiments, the ligand of formula (A) can be in a racemic or optically active form.

As non limiting examples of L2 ligands, one can cite the following ones:

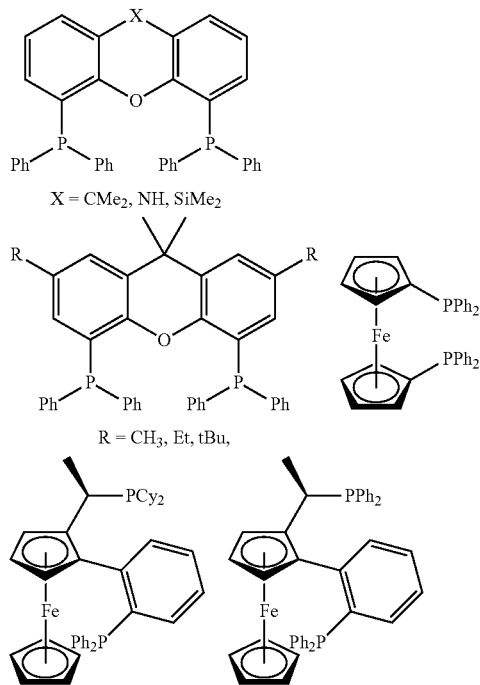

X = CMe$_2$, NH, SiMe$_2$

R = CH$_3$, Et, tBu, wherein Cy represents a cyclohexyl substituted by one or two $C_{1-4}$ alkyl groups, Ph represents a phenyl group optionally substituted by one or two $C_{1-4}$ alkyl groups; said compounds being in an optically active form or in a racemic form, if applicable.

The ligands (A) are all known in the prior art and can be obtained by applying standard general methods which are well known in the state of the art and by the person skilled in the art, e.g. see R. P. J. Bronger, P. C J Kamer, P. W. N. M. van Leeuwen, *Organometallics* 2003, 22, 5358 or R. P. J. Bronger, J. P. Bermon, J. Herwig, P. C. J. Kamer, P. W. N. M. van Leeuwen, *Adv. Synth. Catal.* 2004, 346, 789 or M. Kranenburg, Y. E. M. van der Burgt, P. C. J. Kamer, P. W. N. M. van Leeuwen, K. Goubitz, J. Fraanje *Organometallics* 1995, 14, 3081 or P. Dierkes, P. W. N. M. van Leeuwen *J. Chem. Soc., Dalton Trans.* 1999, 1519. Some of said ligands are even commercially available.

The Rh complex of the invention can be added into the reaction medium of the invention's process in a large range of concentrations. As non-limiting examples, one can cite as complex concentration amounts of complex being greater than 10 ppm, preferably greater than 100 ppm, more preferably greater than 1000 ppm, but less than 50000 ppm, preferably less than 10000 ppm, relative to the amount of substrate. It goes without saying that the optimum concentration of complex will depend, as the person skilled in the art knows, on the nature of the latter, on the nature of the substrate, of the solvent and on the pressure of $H_2$ used during the process, as well as the desired time of reaction.

Useful quantities of base, added to the reaction mixture, may be comprised in a relatively large range. One can cite, as non-limiting examples, amounts of base being greater than 0.1, preferably greater than 1, more preferably greater than 5, but less than 1000, preferably less than 500 molar equivalents, relative to the complex (e.g. base/com=up to 10000).

The complex (1) of the invention can be obtained by applying standard general methods which are well known in the state of the art and by the person skilled in the art. Some of said ligands are even commercially available.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in a stainless steel autoclave otherwise indicated. $H_2$ gas (99.99990%) was used as received. All substrates and solvents were distilled from appropriate drying agents under Ar. NMR spectra were recorded on a Bruker AM-400 ($^1H$ at 400.1 MHz, $^{13}C$ at 100.6 MHz, and $^{31}P$ at 161.9 MHz) spectrometer and normally measured at 300 K, in CDCl$_3$ unless indicated otherwise. Chemical shifts are listed in ppm.

Example 1

Catalytic Hydrogenation of (2E,4E)-4-methyl-5-(p-tolyl)penta-2,4-dienal Using Various Invention Rhodium Complexes (Formation in situ, from [Rh(COD)COD)Cl]$_2$ Precursor with Diphosphines Ligands (La-Ld))

A Typical Experimental Procedure is as Follows:

In a glove box under argon, a glass vial equipped with a teflon-coated magnetic stirring bar was charged with the Rh precursor (e.g. [Rh(COD)Cl]$_2$, 0.005 mmol, 1 mol %), the diphosphine ligand (0.005 mmol, 1 mol %, see Table 1), the optional base (e.g. KOAc, 0.05 mmol, 10 mol %) and CH$_2$Cl$_2$ (1 ml). The solution was then stirred for 1 hour at room temperature. Then a solution of (2E,4E)-4-methyl-5-(p-tolyl)penta-2,4-dienal (0.5 mmol) in CH$_2$Cl$_2$ (1 ml) was added. The vial was then placed in a 75 ml stainless steel autoclave, the autoclave was closed and purged with H$_2$ (6×20 bar) and pressurized with H$_2$ (50 bar) and the solution was stirred at room temperature. After 1 hour, the autoclave was vented and a sample was taken, diluted with MTBE, and the solution was then filtered over a plug of celite 560 and analysed by GC (DB-Wax).

Under these conditions several diphosphines ligands (Table 1) were tested, as reported in Table 2.

TABLE 1

Structure of diphosphine ligands (La-Ld) used

Structure

La
n.b.a. = 95°

TABLE 1-continued

Structure of diphosphine ligands (La-Ld) used

Structure

Ld
n.b.a. = 114° wherein Ph is a $C_6H_5$ group;
n.b.a. means the natural bite angle.

TABLE 2

Hydrogenation of (2E,4E)-4-methyl-5-(p-tolyl)penta-2,4-dienal into (E)-4-methyl-5-(p-tolyl)pent-4-enal with diphosphine (PP, La-Lc), in presence of a base

| N° PP | Rhodium precursor | Com/Base | Base | Time [min] | Conv. % | Sel. % |
|---|---|---|---|---|---|---|
| 1 La | [Rh(COD)Cl]$_2$ | 10000/100000 | KOAc | 60 | 62 | 79 |
| 2 Lb | [Rh(COD)Cl]$_2$ | 10000/100000 | KOAc | 60 | 84 | 42 |
| 3 Lc | [Rh(COD)Cl]$_2$ | 10000/100000 | KOAc | 60 | 100 | 85 |

Wherein COD is 1,5-cyclooctadiene and KOAc is potassium acetate.
Com/Base: molar ratio in ppm relative to the substrate.
Conv. = conversion (in %), analysed by GC of (2E,4E)-4-methyl-5-(p-tolyl)penta-2,4-dienal into any other product (including deconjugated enal, the saturated aldehyde and the alcohol) after the indicated time.
Reaction conditions: $H_2$ gas (50 bar), 25° C., $CH_2Cl_2$ (c.a. 0.25M).
Sel. = selectivity (in %), analysed by GC and calculated as [100 × (E)-4-methyl-5-(p-tolyl)pent-4-enal]/[(E)-4-methyl-5-(p-tolyl)pent-4-enal + of other product].

TABLE 1-continued

Structure of diphosphine ligands (La-Ld) used

Structure

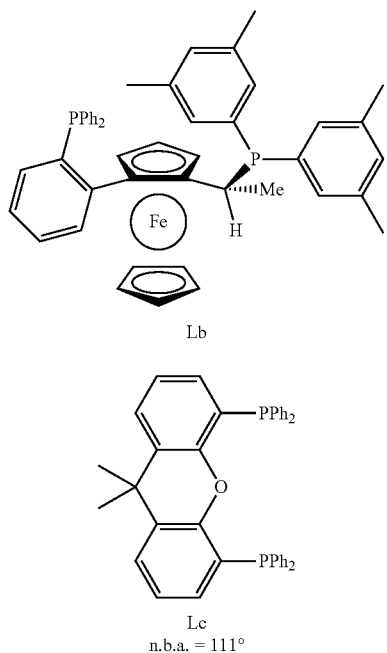

Lb

Lc
n.b.a. = 111°

Example 2

Catalytic Hydrogenation of (2E,4E)-4-methyl-5-(p-tolyl)penta-2,4-dienal Using [Rh(COD)(Ld)][Cl] as Invention Rhodium Complexes (Use of Various Bases)

A Typical Experimental Procedure is as Follows:
In a glove box under argon, a glass vial equipped with a teflon-coated magnetic stirring bar was charged with [Rh(COD)(Ld)][Cl] (0.02 mmol, 1 mol %), the base (0.02 mmol, 1 mol %) and toluene (1 ml). The solution was then stirred for 1 hour at room temperature. Then a solution of (2E,4E)-4-methyl-5-(p-tolyl)penta-2,4-dienal (2 mmol) in toluene (1 ml) was added. The vial was then placed in a 75 ml stainless steel autoclave, the autoclave was closed and purged with $H_2$ (6×20 bar) and pressurized with $H_2$ (30 bar) and the solution was stirred at room temperature. After 90 min, the autoclave was vented and a sample was taken, diluted with MTBE, and the solution was then filtered over a plug of celite 560 and analysed by GC (DB-Wax).
Under these conditions several basic additive were tested, as reported in Table 3.

TABLE 3

Hydrogenation of (2E,4E)-4-methyl-5-(p-tolyl)penta-2,4-dienal into (E)-4-methyl-5-(p-tolyl)pent-4-enal with [Rh(COD)(Ld)][Cl] and a base

| N° | Com/Base | Base | Conv. % | Sel. % |
|---|---|---|---|---|
| 1 | 10000/— | none | 12 | 92 |
| 2 | 10000/10000 | KOAc | 100 | 57 |

TABLE 3-continued

Hydrogenation of (2E,4E)-4-methyl-5-(p-tolyl)penta-2,4-dienal into (E)-4-methyl-5-(p-tolyl)pent-4-enal with [Rh(COD)(Ld)][Cl] and a base

| N° | Com/Base | Base | Conv. % | Sel. % |
|---|---|---|---|---|
| 3 | 10000/10000 | NaOC(O)Ph | 100 | 85 |
| 4 | 10000/10000 | KOC(O)Ph | 100 | 57 |
| 5 | 10000/10000 | Na(acac) | 100 | 83 |
| 6 | 10000/10000 | Na(tBu-acac) | 100 | 92 |
| 7 | 10000/10000 | NaOPh | 100 | 91 |
| 8 | 10000/10000 | NaO(2,6-(tBu)$_2$-4-Me)—C$_6$H$_2$ | 100 | 93 |
| 9 | 10000/10000 | Cs$_2$CO$_3$ | 100 | 80 |

Wherein NaOAc is sodium acetate, KOAc is potassium acetate, NaOC(O)Ph is sodium benzoate, KOC(O)Ph is potassium benzoate, Na(acac) is sodium 4-oxopent-2-en-2-olate, Na(tBu-acac) is sodium 2,2,6,6-tetramethyl-5-oxohept-3-en-3-olate, NaOPh is sodium phenolate, NaO(2,6-(tBu)$_2$-4-Me)—C$_6$H$_2$ is sodium 2,6-di-tert-butyl-4-methylphenolate.
Com/Base: molar ratio in ppm relative to the substrate.
Conv. = conversion (in %), analysed by GC) of (2E,4E)-4-methyl-5-(p-tolyl)penta-2,4-dienal into any other product (including deconjugated enal, saturated aldehyde and alcohol) after the indicated time.
Reaction conditions: H$_2$ gas (30 bar), 25° C., toluene (c.a. 1M), 90 min.
Sel. = selectivity (in %), analysed by GC) and calculated as [100 × (E)-4-methyl-5-(p-tolyl)pent-4-enal]/[(E)-4-methyl-5-(p-tolyl)pent-4-enal + of other product].

Example 3

Catalytic Hydrogenation of (2E,4E)-4-methyl-5-(p-tolyl)penta-2,4-dienal Using [Rh(COD)(Ld)][Cl] as Invention Rhodium Complex Under Various S/C and S/B (Substrate/Complex and Substrate/Base) Ratio A Typical Experimental Procedure is as Follows:

In a glove box under argon, a stainless steel autoclave equipped with a teflon-coated magnetic stirring bar was charged with [Rh(COD)(Ld)][Cl] and the base. Then (2E,4E)-4-methyl-5-(p-tolyl)penta-2,4-dienal (10 g, 54 mmol) in toluene (12.5 ml) was added. The autoclave was closed and purged with H$_2$ (6×20 bar) and pressurized with H$_2$ (30 bar) and the solution was stirred at 60° C. (bath temp.) for the indicated time. Then the autoclave was cooled to room temperature, vented and a sample was taken, diluted with MTBE, the solution was then filtered over a plug of celite 560 and analysed by GC (DB-Wax).

Under these conditions several S/C and S/B ratio were tested, as reported in Table 4.

TABLE 4

Hydrogenation of (2E,4E)-4-methyl-5-(p-tolyl)penta-2,4-dienal into (E)-4-methyl-5-(p-tolyl)pent-4-enal with [Rh(COD)(Ld)][Cl] and a base

| N° | Com/Base | Base | Time [h] | Conv. % | Sel. % |
|---|---|---|---|---|---|
| 1 | 1000/1000 | KOAc | 2 | 99 | 93 |
| 2 | 100/1000 | KOAc | 4 | 98 | 100 |
| 3 | 50/500 | KOAc | 22 | 49 | 100 |
| 4 | 1000/1000 | KOC(O)Ph | 2 | 98 | 96 |
| 5 | 100/1000 | KOC(O)Ph | 4 | 99.5 | 100 |
| 6 | 50/500 | KOC(O)Ph | 22 | 99 | 100 |
| 7 | 1000/1000 | Na(acac) | 2 | 99.5 | 86 |
| 8 | 1000/1000 | Na(tBu-acac) | 2 | 99.5 | 90 |

Wherein NaOAc is sodium acetate, KOAc is potassium acetate, NaOC(O)Ph is sodium benzoate, KOC(O)Ph is potassium benzoate, Na(acac) is sodium 4-oxopent-2-en-2-olate, Na(tBu-acac) is sodium 2,2,6,6-tetramethyl-5-oxohept-3-en-3-olate.
Com/Base: molar ratio in ppm relative to the substrate.
Conv. = conversion (in %), analysed by GC) of (2E,4E)-4-methyl-5-(p-tolyl)penta-2,4-dienal into any other product (including deconjugated enal and the aldehyde) after the indicated time.
Reaction conditions: H$_2$ gas (30 bar), 60° C., toluene (c.a. 4.3M).
Sel. = selectivity (in %), analysed by GC) and calculated as [100 × (E)-4-methyl-5-(p-tolyl)pent-4-enal]/[(E)-4-methyl-5-(p-tolyl)pent-4-enal + of other product].

Example 4

Catalytic Hydrogenation of (2E,4E)-4-methyl-5-(p-tolyl)penta-2,4-dienal Using [Rh(COD)(Lc)][Cl] or [Rh(COD)(Ld)][cl] as Invention Rhodium Complex (Use of Various Solvent)

A Typical Experimental Procedure is as Follows:

In a glove box under argon, a stainless steel autoclave equipped with a teflon-coated magnetic stirring bar was charged with [Rh(COD)(Lc)][Cl] (0.005 mmol, 0.1 mol %), potassium benzoate (0.05 mmol, 1 mol %), (2E,4E)-4-methyl-5-(p-tolyl)penta-2,4-dienal (5 mmol) and the appropriate solvent (5 ml). The autoclave was closed and purged with H$_2$ (6×20 bar) and pressurized with H$_2$ (50 bar) and the solution was stirred at room temperature. After 60 min, the autoclave was vented and a sample was taken, diluted with MTBE, and the solution was then filtered over a plug of celite 560 and analysed by GC (DB-Wax).

Under these conditions, several solvent were tested, as reported in Table 5.

TABLE 5

Hydrogenation of (2E,4E)-4-methyl-5-(p-tolyl)penta-2,4-dienal into (E)-4-methyl-5-(p-tolyl)pent-4-enal with [Rh(COD)(Lc)][Cl] and potassium benzoate in various solvent

| N° | Com/Base | Solvent | Conv. % | Sel. % |
|---|---|---|---|---|
| 1 | 1000/10000 | iPrOH | 100 | 96 |
| 2 | 1000/10000 | AcOEt | 100 | 98 |
| 3 | 1000/10000 | Acetone | 100 | 98 |
| 4 | 1000/10000 | THF | 100 | 97 |
| 5 | 1000/10000 | MTBE | 100 | 98 |
| 6 | 1000/10000 | toluene | 100 | 97 |

Wherein iPrOH is iso-propanol, AcOEt is ethyl acetate, THF is tetrahydrofuran, MTBE is methyl-tert-butyl ether.
Com/Base: molar ratio in ppm relative to the substrate.
Conv. = conversion (in %), analysed by GC) of (2E,4E)-4-methyl-5-(p-tolyl)penta-2,4-dienal into any other product (including deconjugated enal and the aldehyde) after the indicated time.
Reaction conditions: H$_2$ gas (50 bar), 25° C., solvent (1M), 60 min.
Sel. = selectivity (in %), analysed by GC) and calculated as [100 × (E)-4-methyl-5-(p-tolyl)pent-4-enal]/[(E)-4-methyl-5-(p-tolyl)pent-4-enal + of other product].

[Rh(COD)(Ld)][Cl] was also tested using the same protocol, as reported in Table 6.

TABLE 6

Hydrogenation of (2E,4E)-4-methyl-5-(p-tolyl)penta-2,4-dienal into (E)-4-methyl-5-(p-tolyl)pent-4-enal with [Rh(COD)(Ld)][Cl] and potassium benzoate in various solvent

| N° | Com/Base | Solvent | Conv. % | Sel. % |
|---|---|---|---|---|
| 1 | 5000/50000 | iPrOH | 99 | 96 |
| 2 | 5000/50000 | AcOEt | 100 | 92 |
| 3 | 5000/50000 | Acetone | 100 | 90 |
| 4 | 5000/50000 | THF | 100 | 93 |
| 5 | 5000/50000 | MTBE | 100 | 95 |

Wherein iPrOH is iso-propanol, AcOEt is ethyl acetate, THF is tetrahydrofuran, MTBE is methyl-tert-butyl ether.
Com/Base: molar ratio in ppm relative to the substrate.
Conv. = conversion (in %), analysed by GC) of (2E,4E)-4-methyl-5-(p-tolyl)penta-2,4-dienal into any other product (including deconjugated enal and the aldehyde) after the indicated time.
Reaction conditions: H$_2$ gas (10 bar), 25° C., solvent (0.5M), 120 min.
Sel. = selectivity (in %), analysed by GC) and calculated as [100 × (E)-4-methyl-5-(p-tolyl)pent-4-enal]/[(E)-4-methyl-5-(p-tolyl)pent-4-enal + of other product].

Example 5

Catalytic Hydrogenation of (2E,4E)-4-methyl-5-(p-tolyl)penta-2,4-dienal Using Various Invention Rhodium Complexes with Potassium Benzoate as a Base in EtOH Various complexes were also tested using the same protocol as described in Example 4, as reported in Table 7.

TABLE 7

Hydrogenation of (2E,4E)-4-methyl-5-(p-tolyl)penta-2,4-dienal into (E)-4-methyl-5-(p-tolyl)pent-4-enal with various rhodium complexes and potassium benzoate in ethanol

| N° | Com/Base | Rhodium complexes | Conv. % | Sel. % |
|----|----------|-------------------|---------|--------|
| 1  | 1000/10000 | [Rh(COD)(Lc)][Cl]  | 100 | 89 |
| 2  | 1000/10000 | [Rh(NBD)(Lc)][Cl]  | 100 | 93 |
| 3  | 1000/10000 | [Rh(COD)(Lc)][BF$_4$] | 100 | 93 |
| 4  | 1000/10000 | [Rh(COD)(Lc)][TfO]* | 100 | 91 |

Wherein COD is 1,5-cyclooctadiene, NBD is norbornadiene, BF$_4$ is tetrafluoroborate, TfO is trifluoromethanesulfonate.
Com/Base: molar ratio in ppm relative to the substrate.
Conv. = conversion (in (%), analysed by GC) of (2E,4E)-4-methyl-5-(p-tolyl)penta-2,4-dienal into any other product (including deconjugated enal and the aldehyde) after the indicated time.
Reaction conditions: H$_2$ gas (20 bar), 60° C., EtOH (1M), 120 min.
Sel. = selectivity (in (%), analysed by GC) and calculated as [100 × (E)-4-methyl-5-(p-tolyl)pent-4-enal]/[(E)-4-methyl-5-(p-tolyl)pent-4-enal + of other product].
*Generated in-situ from [Rh(COD)$_2$][TfO].

Example 6

Catalytic Hydrogenation of Various Dienal Using [Rh(COD)(Ld)][Cl] as Invention Rhodium Complex A Typical Experimental Procedure is as Follows:

In a glove box under argon, a stainless steel autoclave equipped with a teflon-coated magnetic stirring bar was charged with [Rh(COD)(Ld)][Cl] and potassium benzoate. Then a solution of the appropriate substrate (2.5 mmoles) in a solvent (10 mL) was added. The autoclave was closed and purged with H$_2$ (6×20 bar) and pressurized with H$_2$ (20-25 bar) and the solution was stirred at the indicated temperature for the indicated time. Then the autoclave was cooled to room temperature, vented and a sample was taken, diluted with MTBE, the solution was then filtered over a plug of celite 560 and analysed by GC (DB-Wax).

Under these conditions several dienals (Table 8) were tested, as reported in Table 9.

TABLE 8

Structure of dienals (Da-Dt) used

Structure

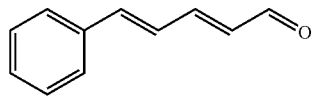

Da

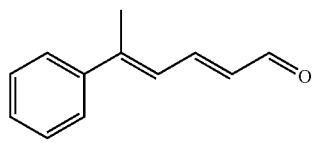

Db

TABLE 8-continued

Structure of dienals (Da-Dt) used

Structure

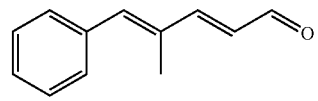

Dc

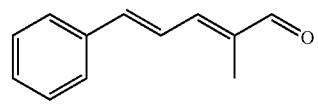

Dd

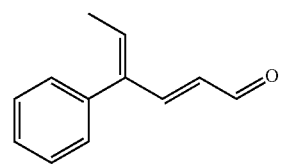

De

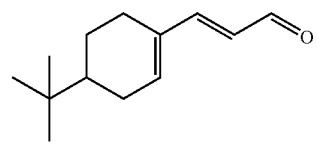

Df

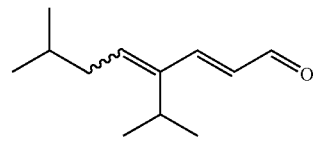

Dg

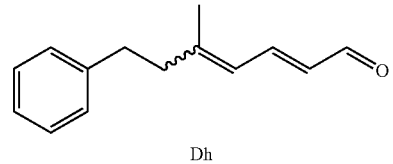

Dh

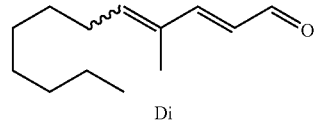

Di

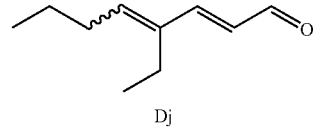

Dj

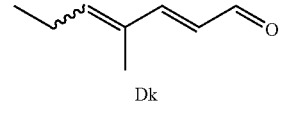

Dk

TABLE 8-continued

Structure of dienals (Da-Dt) used

Structure

Dl

Dm

Dn

Do

Dp

Dq

Dr

Ds

Dt

TABLE 9

Hydrogenation of various dienals (Da-Dt) into their corresponding non-conjugated enal with [Rh(COD)(Ld)][Cl] and a base

| N° | D | Com/Base | Base | Solvent | T [° C.] | Time [h] | Conv. % | Sel. % |
|---|---|---|---|---|---|---|---|---|
| 1* | Da | 10000/50000 | KOAc | $CH_2Cl_2$ | 25 | 1 | 100 | 66 |
| 2* | Da | 10000/50000 | KOC(O)Ph | $CH_2Cl_2$ | 25 | 1 | 100 | 92 |
| 3* | Da | 2000/50000 | KOC(O)Ph | $CH_2Cl_2$ | 25 | 7 | 96 | 85 |
| 4* | Db | 2000/50000 | KOC(O)Ph | $CH_2Cl_2$ | 25 | 7 | 100 | 98 |
| 5* | Dc | 2000/50000 | KOC(O)Ph | $CH_2Cl_2$ | 25 | 7 | 100 | 98 |
| 6* | Dd | 2000/50000 | KOC(O)Ph | $CH_2Cl_2$ | 25 | 7 | 100 | 40 |
| 7* | De | 2000/50000 | KOC(O)Ph | $CH_2Cl_2$ | 25 | 7 | 100 | 96 |
| 8* | Df | 1000/10000 | KOAc | toluene | 25 | 17 | 96 | 91 |
| 9** | Dg | 1000/10000 | KOC(O)Ph | EtOH | 60 | 5 | 100 | 99 |
| 10** | Dh | 1000/10000 | KOC(O)Ph | EtOH | 60 | 5 | 100 | 99 |
| 11** | Di | 1000/10000 | KOC(O)Ph | EtOH | 60 | 5 | 100 | 84 |
| 12*** | Dj | 2000/20000 | KOC(O)Ph | EtOH | 50 | 5 | 100 | 93 |
| 13*** | Dk | 1000/10000 | KOC(O)Ph | EtOH | 50 | 5 | 100 | 88 |
| 14*** | Dl | 1000/10000 | KOC(O)Ph | EtOH | 50 | 5 | 100 | 99 |
| 15** | Dm | 1000/10000 | KOC(O)Ph | EtOH | 60 | 5 | 100 | 94 |
| 16** | Dn | 1000/10000 | KOC(O)Ph | EtOH | 60 | 5 | 100 | 96 |
| 17** | Do | 1000/10000 | KOC(O)Ph | EtOH | 60 | 5 | 100 | 98 |
| 18** | Dp | 1000/10000 | KOC(O)Ph | EtOH | 60 | 2 | 99 | 93 |
| 19** | Dq | 1000/10000 | KOC(O)Ph | EtOH | 60 | 5 | 100 | 99 |
| 20** | Dr | 1000/10000 | KOC(O)Ph | EtOH | 60 | 4 | 100 | 97 |
| 21** | Ds | 1000/10000 | KOC(O)Ph | EtOH | 60 | 5 | 99 | 99 |
| 22** | Dt | 1000/10000 | KOC(O)Ph | EtOH | 60 | 5 | 100 | 68 |

Wherein KOAc is potassium acetate, KOC(O)Ph is potassium benzoate.
Com/Base: molar ratio in ppm relative to the substrate.
Conv. = conversion (in (%), analysed by GC) of the starting dienal into any other product (including deconjugated enal, the saturated aldehyde or the alcohol) after the indicated time.
*Reaction conditions: $H_2$ gas (25 bar), 25° C., $CH_2Cl_2$ (c.a. 0.25-1M).
**Reaction conditions: $H_2$ gas (20 bar), 60° C., EtOH (c.a. 0.5M).
***Reaction conditions: $H_2$ gas (20 bar), 50° C., EtOH (c.a. 0.5M).
Sel. = selectivity (in (%), analysed by GC) and calculated as [100 × 4-enal]/[4-enal + sum of other products].

Comparative Example 1

Comparison of Catalytic Reduction of (2E,4E)-4-methyl-5-(p-tolyl)penta-2,4-dienal (S1) and (E)-4-(2,6,6-trimethylcyclohex-1-en-1-yl)but-3-en-2-one (S2) Using Various Reduction Methods A Typical Experimental Procedure for the Reduction Under H$_2$ Gas is as Follows:

In a glove box under argon, a stainless steel autoclave equipped with a teflon-coated magnetic stirring bar was charged with the desired catalyst, the optional basic additive (0.1 mmol, 1 mol %), (2E,4E)-4-methyl-5-(p-tolyl)penta-2,4-dienal (10 mmol) and toluene (10 ml). The autoclave was closed and purged with H$_2$ (6×20 bar) and pressurized with H$_2$ at the desired pressure and the solution was stirred at the desired temperature. After the indicated time, the autoclave was vented, a sample was taken, diluted with MTBE, and the solution was then filtered over a plug of celite 560 and analysed by GC (DB-Wax).

A Typical Experimental Procedure for the Reduction with Et$_3$SiH is as Follows:

In a glove box under argon, a Schlenck flask equipped with a teflon-coated magnetic stirring bar was charged with the desired catalyst, (2E,4E)-4-methyl-5-(p-tolyl)penta-2,4-dienal (10 mmol) and toluene (10 ml). Then Et$_3$SiH (11 mmol) was added with a syringe and the solution stirred at 50° C. After the indicated time, the solution was cooled to RT, a sample was taken, diluted with MTBE, analysed by GC (DB-1).

Under these conditions different reduction conditions were tested, as reported in Table 10.

As can be noticed, modifying according to the prior art any characteristics of the present invention does not allow to obtain the desired product in useful yields.

What is claimed is:

1. A process for the reduction by hydrogenation, using molecular H$_2$, of a C$_6$-C$_{20}$ conjugated dienal of formula

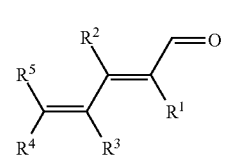

(I)

wherein, when taken separately, each of R$^1$, R$^2$, R$^3$, R$^4$ and R$^5$ represents, independently of each other, a hydrogen atom, a phenyl group optionally substituted or a C$_{1-8}$ alkyl, alkenyl, cycloalkyl or cycloalkenyl group optionally substituted, provided that at least one of said R$^1$, R$^2$, R$^3$, R$^4$ and R$^5$ is not a hydrogen atom; R$^1$ and R$^2$ or R$^2$ and R$^3$ or R$^3$ and R$^4$, when taken together, represent a C$_{3-4}$ alkadienyl or alkenediyl group optionally substituted; R$^1$ and R$^3$ or R$^2$ and R$^5$, when taken together, represent a C$_{2-3}$ alkadienyl or alkenediyl group optionally substituted; R$^4$ and R$^5$, when taken together, represent a C$_{4-5}$ alkadienyl or alkenediyl group optionally substituted;

and the substituents of R$^1$ to R$^5$ are one phenyl group or one, two or three COOR$^7$, OR$^6$ or R$^7$ groups, in which R$^6$

TABLE 10

Reduction of (2E,4E)-4-methyl-5-(p-tolyl)penta-2,4-dienal (S1) and (E)-4-(2,6,6-trimethylcyclohex-1-en-1-yl)but-3-en-2-one (S2) with various reduction methods

| N° | Substrate | Com/Base | Catalyst | Hydride source | Conv. % | Sel. % |
|---|---|---|---|---|---|---|
| | | | Present invention substrate, catalysts and conditions | | | |
| 1 | S1 | 1000/10000 | [Rh(COD)(Lc)][Cl] KOC(O)Ph | H$_2$ (20 bar)* | 100 | 94 |
| 5 | S1 | 1000/10000 | [Rh(COD)(Lc)][Cl] KOC(O)Ph | H$_2$ (50bar)*** | 100 | 97 |
| | | | Present invention substrate and prior art[1)] catalysts and conditions | | | |
| 4 | S1 | 1000/0 | [Rh(PPh$_3$)$_3$Cl] | Et$_3$SiH (1 eq.)** | 0 | — |
| | | | Present invention substrate and conditions and prior art[1)] catalysts | | | |
| 2 | S1 | 1000/0 | [Rh(PPh$_3$)$_3$Cl] | H$_2$ (20 bar)* | 6 | — |
| 3 | S1 | 1000/10000 | [Rh(PPh$_3$)$_3$Cl] KOC(O)Ph | H$_2$ (20 bar)* | 11 | 82 |
| | | | Present invention catalysts and conditions and prior art[1)] substrate | | | |
| 6 | S2 | 1000/10000 | [Rh(COD)(Lc)][Cl] KOC(O)Ph | H$_2$ (50 bar)*** | 6 | — |

Com/Base: molar ratio in ppm relative to the substrate.

Conv. = conversion (in %), analysed by GC) of (2E,4E)-4-methyl-5-(p-tolyl)penta-2,4-dienal into any other product (including deconjugated enal and the aldehyde) after the indicated time.

[1)]Ojima et al. in *Organomet.* 1982, 1390

*Reaction conditions: 50° C., toluene (1M), 120 min.

**Reaction conditions: 50° C., toluene (1M), 18 h.

***Reaction conditions: 25° C., toluene (1M), 60 min.

Sel. = selectivity (in %), analyzed by GC) and calculated as [100 × (E)-4-methyl-5-(p-tolyl)pent-4-enal]/[(E)-4-methyl-5-(p-tolyl)pent-4-enal + of other product].

is a hydrogen atom or a $R^7$ group, $R^7$ representing a $C_{1-4}$ linear or branched alkyl or alkenyl group;
into a deconjugated enal of formula

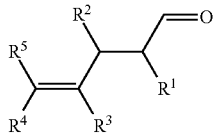  (II)

wherein $R^1$ to $R^5$ are defined as in formula (I);
said process being carried out in the presence of a catalytic system comprising:
at least a base; and
at least one Rh(I) complex obtainable by reacting together:
a $C_{34}$-$C_{60}$ bidentate diphosphine ligand (L2) having a natural bite-angle comprised between 93° and 130°; and
a suitable Rh(I) precursor of formula

[Rh(L)(S)$_v$Y$_r$](Y)$_{1-r}$  or  (1)

[Rh(L)$_2$](Y)  (1')

wherein r is 0 or 1, v is 0, 1 or 2;
L represents a $C_{5-14}$ hydrocarbon diene;
S represents a coordinated molecule of a polar organic solvent or water; and
Y represents a mono-anion.

2. A process according to claim 1, wherein said compound of formula (I) and (II) is a $C_6$-$C_{15}$ compound wherein, when taken separately, each of $R^1$, $R^2$, $R^3$, $R^4$ and $R^5$ represents, independently of each other, a hydrogen atom, a phenyl group optionally substituted or a $C_{1-4}$ alkyl or cycloalkyl group optionally substituted, provided that at least one of said $R^1$, $R^2$, $R^3$, $R^4$ and $R^5$ is not a hydrogen atom; $R^3$ and $R^4$, when taken together, represent a $C_{3-4}$ alkadienyl group optionally substituted; $R^4$ and $R^5$, when taken together, represent a $C_{4-5}$ alkadienyl group optionally substituted.

3. A process according to claim 1, wherein said compound of formula (I) and (II) is a compound wherein $R^1$, $R^2$ represent each a hydrogen atom, $R^3$, $R^4$, $R^5$ represent each a hydrogen atom or a methyl or ethyl group or a cyclohexyl or phenyl group optionally substituted, provided that at least one of said $R^1$, $R^2$, $R^3$, $R^4$ and $R^5$ is not an hydrogen atom; $R^3$ and $R^4$, when taken together, represent a $C_4$ alkadienyl group optionally substituted.

4. A process according to claim 1, wherein said base is an organic or inorganic base having a $pK_a$, of the protonated base of between about 2 and 12.

5. A process according to claim 1, wherein said base is:
as inorganic base an alkaline or $C_{4-16}$ ammonium carbonate or bicarbonate, a basic alox, a siliconate, or an alkaline alkaline-earth or $C_{4-16}$ ammonium fluoride; as organic base an alkaline or $C_{4-16}$ ammonium $C_{2-10}$ carboxylate, or an alkaline or $C_{4-16}$ ammonium $C_{6-10}$ phenolate optionally substituted, an alkaline or $C_{4-16}$ ammonium $C_{5-15}$ 1,3-diketonate, or a $C_{8-10}$ bicyclic amidine.

6. A process according to claim 1, wherein said base is a carbonate, or a fluoride, or a carboxylate or a $C_{5-15}$ 1,3-diketonate or a 5-oxohept-3-en-3-olate, or a phenolate or a naphtholate.

7. A process according to claim 1, wherein said base is sodium acetate, potassium acetate, sodium benzoate, potassium benzoate, sodium (Z)-4-oxopent-2-en-2-olate, sodium (Z)-2,2,6,6-tetramethyl-5-oxohept-3-en-3-olate, sodium phenolate, sodium 2,6-di-tert-butyl-4-methylphenolate, cesium carbonate.

8. A process according to claim 1, wherein said Rh(I) complex is a compound of formula

[Rh(L2)(L)](Y)  (2)

wherein L2, L and Y have the same meaning as in claim 1.

9. A process according to claim 1, wherein L represents a linear or branched $C_5$-$C_{14}$ hydrocarbon compound comprising two carbon-carbon double bonds or a cyclic $C_7$-$C_{14}$ hydrocarbon compound comprising two carbon-carbon double bonds.

10. A process according to claim 1, wherein said Y represents a halide, a $C_{5-15}$ 1,3-diketonate, a $C_1$-$C_8$ alkoxide, OH$^-$, ClO$_4^-$, BF$_4^-$, PF$_6^-$, SbCl$_6^-$, AsCl$_6^-$, SbF$_6^-$, AsF$_6^-$, a $R^dSO_3^{31\ wherein\ Rd}$ is a chlorine of fluoride atom or a $C_1$-$C_8$ alkyl, aryl, fluoroalkyl or fluoroaryl group, or a BR$^e_4^-$ wherein $R^e$ is a phenyl group optionally substituted by one to five groups such as halide atoms and/or methyl and/or CF$_3$ groups.

11. A process according to claim 1, wherein said S represents a $C_{4-7}$ ether, or a $C_{1-4}$ alcohol, or water or N,N-dimethylformamide.

12. A process according to claim 1, wherein said L2 is a compound of formula (R$^b$)$_2$P-Q-P(R$^b$)$_2$  (A)

wherein each $R^b$, taken separately, represents a $C_{6-10}$ aromatic group optionally substituted or a cyclohexyl group optionally substituted, or the two $R^b$ bonded to the same P atom, taken together, represent a 2,2'-oxydiphenyl optionally substituted; and
Q represents a $C_{10}$-$C_{16}$ metallocenediyl optionally substituted or a group of formula
a)

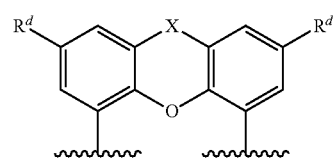  (i)

wherein each $R^d$ represents a hydrogen atom or a $C_{1-8}$ alkyl group, and X represents an oxygen or sulfur atom or a C(R$^{10}$)$_2$, Si(R$^{11}$)$_2$ or NR$^{10}$ group, in which $R^{10}$ is a hydrogen atom or a $R^{11}$ group, $R^{11}$ representing a $C_{1-4}$ linear or branched alkyl group; or
b)

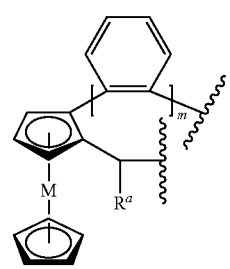  (ii)

in the form of any one of its enantiomers, and wherein m is 0 or 1, M represents Fe or Ru, and $R^a$ represents a hydrogen atom or a $C_{1-4}$ a alkyl group;
and the wavy lines indicate the position of the bond between said Q group and the rest of the compound (A); and
the substituents of $R^b$ are one, two, three or four groups selected amongst the halogen atoms, or $C_{1-10}$ alkoxy, alkyl, alkenyl, or perhalo-hydrocarbon group;
the possible substituents of the metallocenediyl are one $C_{1-4}$ alkyl group or a $CR^{d'}PhN(R^{d''})_2$ group, wherein $R^{d'}$ or $R^{d''}$ are a hydrogen atom or a $C_{1-4}$ alkyl group and Ph is a phenyl group optionally substituted as indicated above for $R^c$.

13. A process according to claim 12, wherein said $R^b$ represent each a $C_{6-10}$ aromatic group optionally substituted or a cyclohexyl group optionally substituted.

14. A process according to claim 12, wherein said Q represents a 1,1'-ferrocenediyl optionally substituted or a group of formula
a)

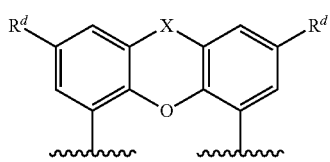

(i)

wherein each $R^d$ represents a hydrogen atom or a $C_{1-4}$ alkyl group, and X represents a) $C(R^{10})_2$, $Si(R^{11})_2$ or $NR^{10}$ group, in which $R^{10}$ is a hydrogen atom or a $R^{11}$ group, $R^{11}$ representing a $C_{1-4}$ linear or branched alkyl group; or b)

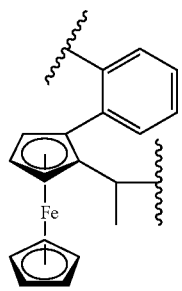

(ii)

in the form of any one of its enantiomers;
the wavy lines indicate the position of the bond between said Q group and the rest of the compound (A).

15. A process according to claim 12, wherein said L2 has a natural bite-angle comprised between 97° and 120°.

16. A process according to claim 6, wherein said base is an acetate, benzoate, acetylacetonate or phenolate.

17. A process according to claim 12, wherein $R^{11}$ represents a methyl group.

18. $R^{11}$ A process according to claim 14, wherein $R^{11}$ represents a methyl group.

* * * * *

UNITED STATES PATENT AND TRADEMARK OFFICE
CERTIFICATE OF CORRECTION

PATENT NO.         : 8,871,982 B2                                   Page 1 of 1
APPLICATION NO.    : 14/000805
DATED              : October 28, 2014
INVENTOR(S)        : Saudan et al.

It is certified that error appears in the above-identified patent and that said Letters Patent is hereby corrected as shown below:

In the Claims

Column 22:
Line 19 (claim 10, line 4), change "$R^dSO_3^{31\ wherein\ Rd}$" to -- $R^dSO_3^-$ wherein $R^d$ --.

Column 23:
Line 32 (claim 14, line 2 after formula (i)), after "represents", change "a)" to -- a --.

Column 24:
Line 30 (claim 18, line 1), after "18.", delete "$R^{11}$".

Signed and Sealed this
Third Day of February, 2015

Michelle K. Lee
*Deputy Director of the United States Patent and Trademark Office*